United States Patent [19]

Flockenhaus et al.

[11] 4,407,974

[45] Oct. 4, 1983

[54] METHOD OF AND APPARATUS FOR CATALYTIC CONVERSION OF GASES

[75] Inventors: Claus Flockenhaus; Erich Hackler; Werner Lommerzheim, all of Essen, Fed. Rep. of Germany

[73] Assignees: Thyssengas GmbH, Duisburg; Didier Engineering GmbH, Essen, both of Fed. Rep. of Germany

[21] Appl. No.: 371,265

[22] Filed: Apr. 23, 1982

Related U.S. Application Data

[60] Continuation of Ser. No. 214,646, Dec. 10, 1980, abandoned, which is a division of Ser. No. 59,522, Jul. 23, 1979, Pat. No. 4,258,006.

[30] Foreign Application Priority Data

Aug. 7, 1978 [DE] Fed. Rep. of Germany ....... 2834589

[51] Int. Cl.$^3$ ................................................ C07C 1/04
[52] U.S. Cl. ..................................... 518/711; 518/712; 518/706
[58] Field of Search .................... 518/711, 712, 706

[56] References Cited

U.S. PATENT DOCUMENTS

| | | | |
|---|---|---|---|
| 2,818,049 | 12/1957 | Blaskowski et al. | 122/4 D X |
| 2,852,545 | 9/1958 | Jenny | 518/712 |
| 3,277,651 | 10/1966 | Augsburger | 60/679 |
| 3,351,564 | 11/1967 | Faatz et al. | 518/712 |
| 4,116,005 | 9/1978 | Willyoung | 60/655 |
| 4,160,805 | 7/1979 | Inaba et al. | 122/4 D X |
| 4,223,529 | 9/1980 | Willyoung | 122/4 D X |

FOREIGN PATENT DOCUMENTS 643606 9/1950 United Kingdom .

*Primary Examiner*—Howard T. Mars
*Attorney, Agent, or Firm*—Toren, McGeady and Stanger

[57] ABSTRACT

A method of catalytic conversion of feed gases, particularly of a low-sulphur gas mixture rich in carbon monoxide and hydrogen, into a product gas mixture containing methane and/or higher hydrocarbons under high pressure includes the step of removing heat of reaction from the catalytic conversion from a reaction zone by feeding both water and steam to form a cooling medium through a pipe coil in the reaction zone. This forms superheated steam in the pipe coil and the superheated steam is then converted into another form of energy, for example in a turbo-generator. Preferably the reaction zone is a fluidized bed. For carrying out this method a reactor is used, which is preferably a fluidized bed reactor and in this reactor the piping system forming the superheater is disposed in the lower part of the reaction zone. The superheater is connected to a feedwater line and to a steam inlet line and a steam turbine is connected to a steam output line leading from the superheater.

5 Claims, 1 Drawing Figure

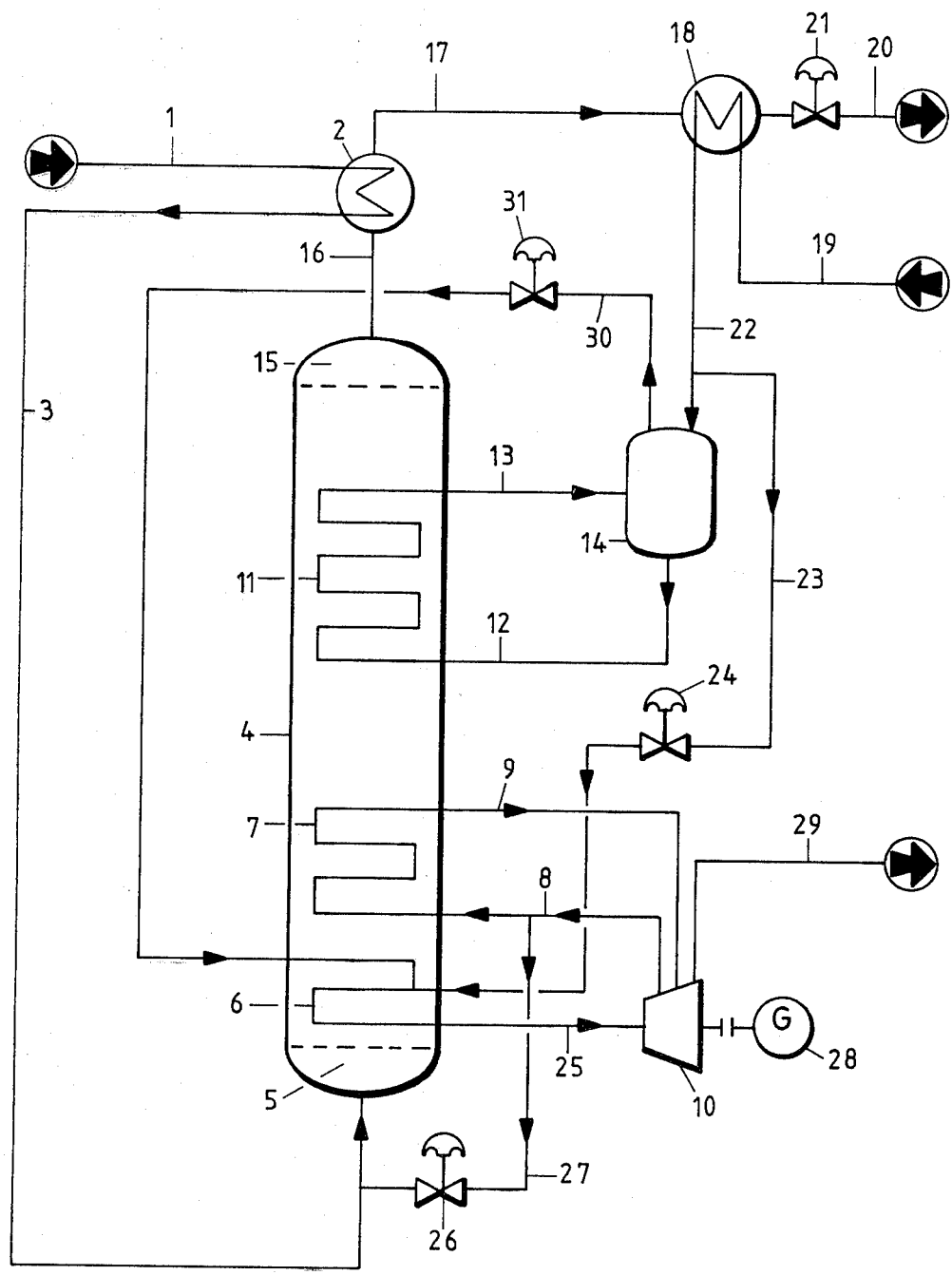

METHOD OF AND APPARATUS FOR CATALYTIC CONVERSION OF GASES

This is a continuation application of Ser. No. 214,646 filed Dec. 10, 1980 now abandoned, which, in turn, was a division of application Ser. No. 059,522 filed July 23, 1979 now U.S. Pat. No. 4,258,006.

This invention relates to methods of catalytic conversion of feed gases, especially low-sulphur gas mixtures rich in carbon monoxide and hydrogen, into a product gas containing methane and/or higher hydrocarbons under high pressure, wherein the heat of the catalytic conversion reaction is removed from a reaction zone with the assistance of an evaporating cooling medium.

In a known method such as this, the feed gas, which contains hydrogen, carbon monoxide, carbon dioxide and nitrogen is conducted through a methanization zone of a fluidized bed reactor. The methanization zone may consist of several stages. In a two-stage methanization zone, the following main reactions take place in a pre-methanization stage and an aftermethanization stage:

$$CO + 3H_2 \rightarrow CH_4 + H_2O; \text{ and}$$

$$CO + H_2O \rightarrow CO_2 + H_2$$

These reactions take place exothermally, so that in order to avoid excessive temperatures in the methanization zone some cooling must be provided.

This cooling is effected with cooling water which becomes heated in a cooler and is generally converted into steam. The material is either re-cooled outside the fluidized bed or is supplied as steam to a steam consumer. As described in German Patent Application R 8174 IVc/26a, a cooling system composed of tubes may serve for removing the reaction heat.

In high-pressure methanization it is of importance to recover and utilize the heat of reaction. Since the reaction heat released in methanization in any case amounts to about 25% of the heat value of the methane produced, methods of producing methane and higher hydrocarbons are increasingly important according to the thermal efficiency at which the reactors can be operated.

The object of the present invention now is to provide a method in which the reaction heat generated in methanization is converted into other forms of energy with as high as possible a thermal efficiency.

To this end the present invention consists in a method of catalytic conversion of feed gases into a product gas mixture containing methane and/or higher hydrocarbons under high pressure, heat of reaction from the catalytic conversion being removed from a reaction zone with the assistance of a cooling medium, which is evaporated, wherein the cooling medium in the form of feedwater and steam are introduced into the reaction zone through piping systems and are superheated and then the superheated steam is converted into another form of energy.

The steam is superheated in the zone of highest reaction heat production. In this way not only are the temperatures required in the reaction zone maintained in an effective manner, but the reaction heat is utilized to an optimum extent. Moreover, a further advantage arises for the gas reaction by the fact that this zone is operated at a higher temperature on the gas side of the piping systems.

The invention consequently represents a substantial contribution to the effective utilization of the heat released in methanization. By an appropriate regulation of flow rate of the cooling medium it is possible, for example, in the methanization process to maintain a temperature of 820° K. in the hottest zone and to utilize the superfluous heat potential for the superheating of steam.

The steam may be partially expanded in the energy conversion and can then be reheated after the zone of maximum reaction heat production and then again be supplied to the energy conversion apparatus. Furthermore, a portion of the steam which has been partially expanded in the energy conversion can be conducted into the reaction zone which may be for example, in the form of a fluidized bed. In this way the steam required for the gas reaction is provided in a simple manner.

In order to achieve further heat utilization when carrying out the method in accordance with the invention, the feedstock gas mixture may be heated by the product gas mixture in a heat exchanger. In the same manner the feedwater may be heated by the product gas in a heat exchanger.

In accordance with another aspect of the invention, in carrying out the method in accordance with the invention a reactor is used, means including a feed gas line supply feed gases to the reactor, means including a product gas line withdraw product gas from the reactor and further means form a reaction zone in the reactor, the reaction zone has an upper part and a lower part, wherein a piping system forming a superheater is disposed in the lower part of the reaction zone, the superheater is connected to a feedwater line and a steam inlet line, and a steam turbine is connected to a steam output line leading from the superheater.

In a preferred embodiment of the invention, the reactor may also be constructed as a fluidized bed reactor. By superheating the steam in the reactor, the steam can be considerably better utilized in a steam turbine or in other steam consumers in which the conversion into other forms of energy takes place. On account of the high temperatures occurring in methanization, of for example 820° K., the superheat surfaces can be relatively small by comparison with normal flue gas superheat surfaces, since the α-values in fluidized beds at the gas side are about 500 W/m².

Above the steam superheater, a superheating reheater may be mounted. This may be connected to a turbine for the purpose of superheat reheating of steam which has been partly expanded in the turbine. In this way the reaction heat can be especially favourably used.

Since the reaction heat is especially intense at the feed gas inlet to the reactor, the feedwater which is preheated via a feedwater line can, in accordance with a preferred feature of the invention, be sprayed into the steam in the steam superheater.

A further evaporator coil for boiler water can be disposed, for the further removal of reaction heat, before, between or after the superheater coils. Thus a heat exchanger coil may be situated in the upper region of the fluidized bed reactor, this coil being connected by two pipes to a steam drum, which is connected by a steam line to the steam superheater and is also connected to the feedwater line. In this way it is possible to supply the steam superheater with steam and to regulate the steam temperature.

With advantage, a line leading into the feed gas line branches from the steam line for the partially expanded steam leading to the reheater. Through this line the steam necesssary for the methanization reaction is introduced into the fluidized bed reactor or other reaction zone.

Furthermore, both the product gas line and also the feed gas line may pass through a heat exchanger. In this way it is possible simultaneously to cool the product gas and to heat the feed gas. For similar reasons, both the product gas line and also the feedwater line may pass through a further heat exchanger. In this way it is possible to cool the product gas still further and simultaneously to heat the feedwater.

An example of a method in accordance with the invention will now be described with reference to the accompanying drawing which is a flow diagram.

A feed gas mixture of hydrogen, carbon monoxide, carbon dioxide and nitrogen flows through a feed gas line 1 into a heat exchanger 2, in which it is heated to a temperature of 500° K. The heated feed gas leaves the heat exchanger 2 at a pressure of 60 bar and flows through a line 3 from below into a fluidized bed reactor 4. In a lower space 5 of the fluidized bed reactor 4 reaction heat produces a temperature for example of 820° K. In the reaction space 5 there is a steam superheater 6, in which, for the stated reaction temperature, a steam temperature of about 750° K. can be reached.

Above the steam superheater 6 there is a reheater 7, connected via lines 8 and 9 to a steam turbine 10. In the upper region of the fluidized bed reactor 4 there is a heat exchanger coil 11, which is connected via lines 12 and 13 to a steam drum 14. With the help of the heat exchanger coil 11 the reaction in the upper region 15 of the fluidized bed reactor 4 can be maintained at a temperature of about 525 K.

Product gas, also at a pressure of 60 bar, leaves the upper end of the fluidized bed reactor 4 through a product gas line 16, which conducts the product gas through the heat exchanger 2, in which it is cooled with simultaneous heating of the feed gas mixture. The product gas leaves the heat exchanger 2 through a line 17 and passes thence into a further heat exchanger 18, in which it is cooled by simultaneous heating of feedwater entering through a line 19, and is then conducted through a line 20 for use in further treatment. In the line 20 there is a regulator 21 which maintains a pressure of about 60 bar in the lines 16, 17 and consequently also in the fluidized bed reactor and also in the feedstock gas lines 1 and 3.

Through a line 19, which passes through the heat exchanger 18 and leaves the latter as a pressure line 22, the steam drum 14 is supplied with feedwater. An injection spray line 23 branches from the line 22 and leads through a valve 24 to the steam superheater 6.

In order to maintain the desired steam temperature at an outlet line 25 from the steam superheater 6, feedwater is sprayed via the injection line 23 into the steam superheater 6. In this way the temperature or flow rate of steam supplied via the line 25 to the turbine 10 can be regulated. At the steam turbine 10 steam at low pressure is conducted via the line 8 to a reheater 7 situated after the steam superheater 6 in the fluidized bed reactor 4 and is conducted after being superheated, through the line 9 for further utilization to the turbine 10. From the line 8, the steam necessary for the reaction in the fluidized bed reactor 4 is supplied by means of a regulator 26 via a steam line 27 into the feed gas line 3. The exhaust steam from the turbine 10 which drives an electrical generator 28 can be supplied via a line 29 to various consumers, not shown in the drawing, as heating steam or can be condensed.

Further reaction heat can be removed from the fluidized bed reactor 4 by means of the heat exchanger coil 11. The heat exchanger coil 11 is connected via the lines 12 and 13 to the steam drum 14. The line 12 conducts boiler water from the steam drum 14 into the heat exchanger coil 11, whereas the line 13 returns the steam-water mixture to the steam drum 14. The pressure in the steam drum 14 is maintained, for example, at 90 bar. The steam required for the steam superheater 6 is supplied via a line 30 fitted with a regulator 31.

We claim:

1. In a method of catalytically converting feed gases comprising hydrogen and carbon monoxide into a mixture containing hydrocarbon gases under high pressure within an upwardly extending fluidized bed reactor, and including removing by means of an evaporable cooling medium the heat of reaction from said catalytic conversion in the reactor from a reaction zone located in the fluidized bed which zone is elongated in the direction of the flow of the feed gases therethrough from a gas inlet at the lower end to a gas outlet at the upper end of the reaction zone, the improvement comprising that said cooling medium is in the form of feedwater and steam and comprising the steps of introducing pressurized feedwater from a closed space exterior of the reaction zone into the reaction zone at a first location spaced from the inlet end of the reaction zone and flowing the feedwater in indirect heat transfer relation with the gases flowing through the first location in the reaction zone for maintaining the temperature in the first location of the reaction zone approximately 300° K. below the temperature at a second location adjacent the inlet to the reaction zone, and at least partially vaporizing the feedwater in the first location, returning the at least partially vaporized feedwater back to the closed spaced after its passage through the reaction zone, withdrawing the steam in the at least partially vaporized feedwater from the closed space and introducing the steam along with feedwater from a supply source into the reaction zone at the second location adjacent to the inlet end and superheating the steam and feedwter as it flows in indirect heat transfer relation with the gases flowing through the second location of the reaction zone for maintaining the temperature in the second location of the reaction zone approximately 300° K. above the temperature at the first location, removing the superheated steam from the reaction zone and converting said superheated steam into another form of energy at a location spaced from the reactor, reheating the superheated steam, which is partially expanded in said energy conversion, by conveying the partially expanded steam back from the location spaced from the reactor into the reaction zone at a third location within the reaction zone positioned between the second location where superheating takes place and the first location where at least partial vaporization takes place and flowing the partially expanded steam in indirect heat transfer relation with the gases flowing through the reaction zone and then removing said reheated steam from the reaction zone and converting said reheated steam to another form of energy, and conducting a portion of said steam being conveyed to the third location, which has been partially expanded in the course of said energy conversion, into said reaction zone in direct heat transfer with the feed gases flowing through the gas inlet into said reaction zone to form a reaction steam in said catalytic conversion.

2. A method as claimed in claim 1, further comprising the step of heating said feed gases by said product gas mixture by indirect heat exchange after the product gas mixture exits from the outlet end of said reaction zone.

3. A method as claimed in claim 1, further comprising the step of preheating said feedwater by said product gas mixture by indirect heat exchange after the product gas mixture exits from the outlet end of said reaction zone.

4. A method cas claimed in claim 1, in which said feed gases comprise a low-sulphur gas mixture rich in carbon monoxide and hydrogen.

5. In a method of catalytically converting feed gases comprising hydrogen and carbon monoxide into a mixture containing hydrocarbon gases under high pressure within an upwardly extending fluidized bed reactor, and including removing by means of an evaporable cooling medium the heat of reaction from said catalytic conversion in the reactor from a reaction zone located in the fluidized bed which is elongated in the direction of the flow of the feed gases therethrough from a gas inlet at the lower end to a gas outlet at the upper end of the reactor, the improvement comprising that said cooling medium is in the form of feedwater and steam and comprising the steps of introducing feed gases into the gas inlet at a temperature of 500° K. and a pressure of 60 bar, introducing pressurized feedwater from a closed space exterior of the reaction zone into the reaction zone at a first location spaced from the inlet end of the reaction zone where the temperature in the reaction zone is about 525° K. and flowing the feedwater in indirect heat transfer relation with the gases flowing through the first location in the reaction zone for maintaining the temperature in the first location of the reaction zone significantly below the temperature at a second location adjacent the inlet to the reaction zone where the temperature is 820° K., and at least partially vaporizing the feedwater in the first location, returning the at least partially vaporized feedwater back to the closed space after its passage through the reaction zone, withdrawing the steam in the at least partially vaporized feedwater from the closed space and introducing the steam along with feedwater from a supply source into the reaction zone at the second location adjacent to the inlet end and superheating the steam and feedwater as it flows in indirect heat transfer relation with the gases flowing through the second location of the reaction zone for maintaining the temperature in the second location of the reaction zone at 820° K. significantly above the temperature at the first location, spraying the feedwater into the steam flowing in indirect heat transfer relation with the second location in the reaction zone from maintaining the steam temperature at the outlet from the second location at about 750° K., removing the superheated steam from the reaction zone and converting said superheated steam into another form of energy at a location spaced from the reactor, reheating the superheated steam, which is partially expanded in said energy conversion, by conveying the partially expanded steam back into the reaction zone at a third location positioned between the second location where superheating takes place and the first location where at least partial vaporization takes place and flowing the partially expanded steam in indirect heat transfer relation with the gases flowing through the reaction zone and then removing said reheated steam from the reaction zone and converting said heated steam to another form of energy, and conducting a portion of said steam being conveyed to the third location, which has been partially expanded in the course of said energy conversion, into said reaction zone in direct heat transfer with the feed gases flowing through the gas inlet into said reaction zone to form a reaction steam in said catalytic conversion.

* * * * *